United States Patent
Jackson et al.

[11] Patent Number: 6,082,990
[45] Date of Patent: Jul. 4, 2000

[54] STENT CRIMPING TOOL

[75] Inventors: Gregg A. Jackson; Stephen A. Morales, both of Mountain View, Calif.

[73] Assignee: Advanced Cardiovascular Systems, Inc., Santa Clara, Calif.

[21] Appl. No.: 09/024,910

[22] Filed: Feb. 17, 1998

[51] Int. Cl.[7] .................................................. B29C 55/22
[52] U.S. Cl. ........................ 425/517; 425/329; 425/392; 425/DIG. 5; 264/249; 72/189; 72/194; 29/517; 29/283.5
[58] Field of Search ............................ 264/249; 425/329, 425/391, 392, DIG. 5, 517; 606/1, 108; 29/282, 516, 283.5, 515, 517, 518; 72/189, 194

[56] References Cited

U.S. PATENT DOCUMENTS

| | | | |
|---|---|---|---|
| 3,439,519 | 4/1969 | Gerding | 72/189 |
| 4,468,224 | 8/1984 | Enzmann et al. . | |
| 4,538,440 | 9/1985 | Kottke | 72/189 |
| 4,576,142 | 3/1986 | Schiff . | |
| 4,644,936 | 2/1987 | Schiff . | |
| 4,681,092 | 7/1987 | Cho et al. . | |
| 4,697,573 | 10/1987 | Schiff . | |
| 4,703,546 | 11/1987 | Gilbert | 29/157.1 R |
| 4,901,707 | 2/1990 | Schiff . | |
| 5,183,085 | 2/1993 | Timmermans . | |
| 5,207,960 | 5/1993 | Moret De Rocheprise | 264/103 |
| 5,546,646 | 8/1996 | Williams et al. . | |
| 5,626,604 | 5/1997 | Cottone, Jr. . | |
| 5,630,830 | 5/1997 | Verbeek | 606/198 |
| 5,653,691 | 8/1997 | Rupp et al. . | |
| 5,658,181 | 8/1997 | Brown, II | 445/23 |
| 5,672,169 | 9/1997 | Verbeek . | |
| 5,715,723 | 2/1998 | Owens . | |
| 5,738,674 | 4/1998 | Williams et al. . | |
| 5,746,764 | 5/1998 | Green et al. . | |
| 5,783,227 | 7/1998 | Dunham . | |
| 5,785,715 | 7/1998 | Schatz . | |
| 5,836,952 | 11/1998 | Davis et al. . | |
| 5,860,966 | 1/1999 | Tower | 606/1 |
| 5,911,452 | 6/1999 | Yan | 29/516 |

FOREIGN PATENT DOCUMENTS

| | | |
|---|---|---|
| 2 088 811 | 6/1982 | United Kingdom . |
| WO 98/14120 | 4/1998 | WIPO . |
| WO 98/19633 | 5/1998 | WIPO . |

OTHER PUBLICATIONS

U.S. Application No. 08/795,335 filed Feb. 4, 1997.
U.S. Application No. 08/837,771 filed Apr. 22, 1997.
U.S. Application No. 08/089,936 filed Jul. 15, 1997.
U.S. Application No. 08/962,632 filed Nov. 3, 1997.

*Primary Examiner*—Jan H. Silbaugh
*Assistant Examiner*—Stefan Staicovici
*Attorney, Agent, or Firm*—Fulwider Patton Lee & Utecht, LLP

[57] ABSTRACT

A stent crimping tool for firmly and uniformly crimping a stent onto a balloon catheter. The stent crimping tool is constructed of three orthogonally arranged semi-circular shaped cams rotatably mounted on a common base. Two cams are disposed horizontally side-by-side and one cam is vertically disposed. Rotation of the three cams is synchronized by interacting racks on each cam. A groove is formed into the outer circumference of each cam and the three cams are arranged on the base, which also includes a groove, to collectively form an axial space in which a stent-catheter assembly is inserted. Rotation of the cams draws the uncrimped stent and catheter into the axial space in which the stent is crimped onto the balloon catheter by the compressive forces exerted by the grooves of the cams and the base.

25 Claims, 5 Drawing Sheets

STENT CRIMPING TOOL

BACKGROUND OF THE INVENTION

The present invention relates to an apparatus for loading a tubular graft, such as a stent, onto the distal end of a catheter assembly of the kind used, for example, in percutaneous transluminal coronary angioplasty (PTCA) or percutaneous transluminal angioplasty (PTA) procedures.

In typical PTCA procedures, a guiding catheter is percutaneously introduced into the cardiovascular system of a patient through the brachial or femoral arteries and advanced through the vasculature until the distal end of the guiding catheter is in the ostium. A guide wire and a dilatation catheter having a balloon on the distal end are introduced through the guiding catheter with the guide wire sliding within the dilatation catheter. The guide wire is first advanced out of the guiding catheter into the patient's coronary vasculature and the dilatation catheter is advanced over the previously advanced guide wire until the dilatation balloon is properly positioned across the arterial lesion. Once in position across the lesion, a flexible and expandable balloon is inflated to a predetermined size with a radiopaque liquid at relatively high pressures to radially compress the atherosclerotic plaque of the lesion against the inside of the artery wall and thereby dilate the lumen of the artery. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

In angioplasty procedures of the kind referenced above, restenosis of the artery may develop over time, which may require another angioplasty procedure, a surgical bypass operation, or some other method of repairing or strengthening the area. To reduce the likelihood of the development of restenosis and to strengthen the area, a physician can implant an intravascular prosthesis for maintaining vascular patency, commonly known as a stent, inside the artery at the lesion. The stent is crimped tightly onto the balloon portion of the catheter and transported in its delivery diameter through the patient's vasculature. At the deployment site, the stent is expanded to a larger diameter, often by inflating the balloon portion of the catheter. The stent also may be of the self-expanding type.

Since the catheter and stent travel through the patient's vasculature, and probably through the coronary arteries, the stent must have a small delivery diameter and must be firmly attached to the catheter until the physician is ready to implant it. Thus, the stent must be loaded onto the catheter so that it does not interfere with delivery, and it must not come off the catheter until it is implanted.

In procedures where the stent is placed over the balloon portion of the catheter, it is necessary to crimp the stent onto the balloon portion to reduce its diameter and to prevent it from sliding off the catheter when the catheter is advanced through the patient's vasculature. Non-uniform crimping can result in sharp edges being formed along the now uneven surface of the crimped stent. Furthermore, non-uniform stent crimping may not achieve the desired minimal profile for the stent and catheter assembly. Where the stent is not reliably crimped onto the catheter, the stent may slide off the catheter and into the patient's vasculature prematurely as a loose foreign body, possibly causing obstructed arteries, blood clots in the vasculature, including thrombosis. Therefore, it is important to ensure the proper crimping of a stent onto a catheter in a uniform and reliable manner.

This crimping is often done by hand, which can be unsatisfactory due to the uneven application of force resulting in non-uniform crimps or loosely fitted stents which pose a critical danger to the patient. In addition, it is difficult to visually judge when a uniform and reliable crimp has been applied.

Some self-expanding stents are difficult to load by hand onto a delivery device such as a catheter. Furthermore, the more the stent is handled the higher the likelihood of human error, which would be antithetical to a properly crimped stent. Accordingly, there is a need in the art for a device for reliably crimping a stent onto a catheter.

There have been attempts at devising a tool for crimping a stent onto a balloon delivery catheter. An example of such a tool comprises a series of plates having substantially flat and parallel surfaces that move in a rectilinear fashion with respect to each other. A stent carrying catheter is disposed between these surfaces, which surfaces crimp the stent onto the outside of the catheter by their relative motion and applied pressure. The plates have multiple degrees of freedom and may have force-indicating transducers to measure and indicate the force applied to the catheter during crimping of the stent.

Another stent loading tool design is comprised of a tubular member housing a bladder. The tubular member and bladder are constructed to hold a stent that is to be crimped onto a balloon catheter assembly. Upon placement of the stent over the balloon portion of the catheter, a valve in the loading tool is activated to inflate the bladder. The bladder compresses the stent radially inward to a reduced diameter onto the balloon portion of the catheter to achieve a snug fit. In this way, the stent is crimped onto the distal end of a balloon catheter with a minimum of human handling. The foregoing stent crimping tools are disclosed in, for example, U.S. Pat. Nos. 5,437,083 and 5,546,646 to Williams et al.

Yet another stent crimping tool is known in the art as the BARD XT, which is actually a stent loader. It is constructed from a rigid, tubular body with a ball at one end connected to a plurality of long, thin strips passing through the tubular body. An uncrimped stent is placed over the plurality of long, thin strips, which hold the stent in an expanded state. The balloon portion of a catheter is inserted into the cylindrical space formed by the plurality of strips. When the user pulls the ball while holding the tubular body against the stent, the strips are slid from beneath the stent and the stent is transferred onto the balloon portion.

Still another conventional stent crimping tool is manufactured by JOHNSON & JOHNSON and appears similar to a hinged nutcracker. Specifically, the tool is comprised of two hand operated levers hinged at one end and gripped in the palm of the hand at the opposite end. A cylindrical opening holding a crimping tube is provided through the mid-portion of the tool to receive therein a stent loaded onto a balloon catheter. The crimping operation is performed by the user squeezing the handle thereby pressing the crimping tube which in turn pinches the stent onto the balloon catheter.

While the prior art devices are suitable for crimping stents onto balloon catheters, they suffer from problems such as non-uniform crimping forces, resulting in non-uniform crimps. Consequently, they are unsuitable for use by physicians in a cath lab who desire to crimp the stent onto the balloon catheter.

SUMMARY OF THE INVENTION

Both PTCA and PTA procedures have become commonplace in treating stenoses or lesions in blood vessels and coronary arteries. In approximately 35% to 40% of the procedures, restenosis may develop requiring a further angioplasty, atherectomy or bypass procedure to return the patency of the vessel. Intravascular stents are now being deployed after PTCA and PTA procedures, and after atherectomies, in order to help prevent the development of restenosis. Importantly, such stents, mounted on the balloon portion of a catheter, must be tightly crimped to provide a low profile delivery diameter, and to ensure that the stent stays on the balloon until the balloon is expanded and the stent is implanted in the vessel. The present invention is directed to a crimping tool that can repeatedly provide a uniform and tight crimp to ensure the low profile diameter of the stent on the balloon portion of the catheter, and to ensure that the stent remains firmly attached until it is implanted in the vessel by expanding the balloon.

More precisely, the present invention is directed to a tool for crimping a stent onto a balloon catheter comprising a base having a central groove, first and second semi-circular cams that rotate side-by-side within a common horizontal plane, wherein the cams include parallel first and second tangents located at a minimum distance between the cams, wherein each cam is rotatably supported in an overlying position above the base, and wherein each cam has a groove at a respective outer circumference. The present invention crimping tool further includes a vertically disposed third cam contained in a vertical plane intersecting the horizontal plane containing the first and second cams, wherein the third cam includes a third tangent parallel to the first and second tangents located at a minimum distance from the first and second cams, and wherein the third cam is rotatably attached to and overlying the base, and further engages the first and second cams at a circumference. The third cam also includes a groove at an outer circumference.

The present invention crimping tool further provides that the grooves of the cams and in the base collectively form an axial space co-extensive with the parallel first, second, and third tangents, whereby the stent loaded onto the balloon catheter is inserted into the axial space and rotation of the cams collectively crimp the stent onto the catheter.

In the preferred embodiment, the first and second cams each have toothed racks at a circumference on a top surface, and the third cam includes toothed racks at a circumference on one side and on an obverse side. So that the three cams move synchronously, the toothed rack of the third cam on one side engages the toothed rack of the first cam, and the toothed rack on the obverse side engages the toothed rack of the second cam.

Accordingly, the coordinated rotation of the cams of the present invention crimp the stent onto the balloon catheter as it feeds through the respective grooves defining the axial space. Two of the side-by-side, horizontal cams are spaced apart such that they can optionally be driven by the user's thumb and forefinger. In the alternative, the horizontal cams can be driven by finger pressure on the third, vertical cam. In other words, the third cam is geared to be driven by the first two side-by-side cams, or vice versa.

The cams are preferably positioned orthogonally to one another. Also, the two horizontal cams are preferably moon-shaped with semi-circular edges having the grooves described above.

The groove or slot at the outer circumference of each cam and in the base is preferably a quarter circle in cross-sectional shape. Those cross-sections complement each other to collectively form a complete circle when the partial grooves of the three cams and the base plate are combined at the intersection of the cams and the base. This intersection is where the parallel tangents of each cam are at their minimal distances apart; it coincides with the axial space where the stent crimping and the final sizing of the stent occur.

The present invention is preferably used in the following process. An uncrimped stent is placed on the balloon catheter slightly distal of where it is intended to be crimped. In most cases, this is approximately 1 to 1.5 millimeters. A mandrel is placed in the balloon catheter before the crimping process begins. Next, the balloon catheter and stent are advanced together toward the axial space created by the intersection of the cam grooves and the raised groove of the base. The slightest resistance felt by the user's fingers on the cams indicates that the stent has interfaced with the cams and has begun to deform.

Next, the user holding the balloon catheter and stent in one hand continues to squeeze with the other the outward most edges of the cams together causing them to rotate further. This rotation advances the balloon catheter and stent into the axial space, which has a smaller diameter than the uncrimped stent. While the stent-catheter assembly is drawn into the axial space, the user can see the stent being crimped or pinched down onto the balloon catheter as each cam exerts radial compressive pressure on the stent.

The cams are rotated until the balloon catheter and stent have passed completely through the axial space and can move freely. The free movement signals that the stent surface is no longer in contact with the cam surface, or more precisely, the groove surface of the cams. The stent crimping process is thus complete.

Of course, the crimping process can be repeated over and over. Each pass of the stent-catheter assembly through the axial space ensures homogeneous and consistent crimping of the stent. The stent can also be rotated about its longitudinal axis while it is pushed and pulled through the axial space.

In an alternative embodiment, the opposing cams may be biased together to continuously apply a crimping force on the stent and balloon catheter as the assembly passes through the axial space. In this alternative embodiment with a spring compliance mechanism, the crimping pressure is continuous due to the force from tension or compression springs, torsion springs, or elastic bands that bias the opposed cams together. So repeated passes through the axial space between the pinching cams continuously deform and reduce the diameter of the stent to that which is smaller than the radius of the grooves in the cams. The limit is reached when the radial forces encounter the mandrel, which resists further deformation and resultant decreases in the stent diameter.

The present invention tool is thus capable of homogeneously and precisely crimping a stent onto a balloon catheter. Such a crimping tool is highly useful to cardiologists and radiologists, for example. Such physicians are constantly concerned with proper deployment of the stent within the patient that it is desirable to have a consistently and reliably crimped stent. The present invention tool is further a time saver, because the stent crimping procedure can be performed fairly efficiently and quickly. Indeed, these and other advantages of the present invention will become apparent from the following detailed description thereof when taken in conjunction with the accompanying exemplary drawings.

BRIEF DESCRIPTION OF THE DRAWINGS

FIGS. 5A and 5B are a side elevational and a plan view, respectively, of a preferred embodiment cam, and FIG. 5C further provides an enlarged detail view of a preferred embodiment groove.

FIG. 6 is a side elevational view of a preferred embodiment base showing the raised groove.

DETAILED DESCRIPTION OF THE PREFERRED EMBODIMENTS

Figure 1:
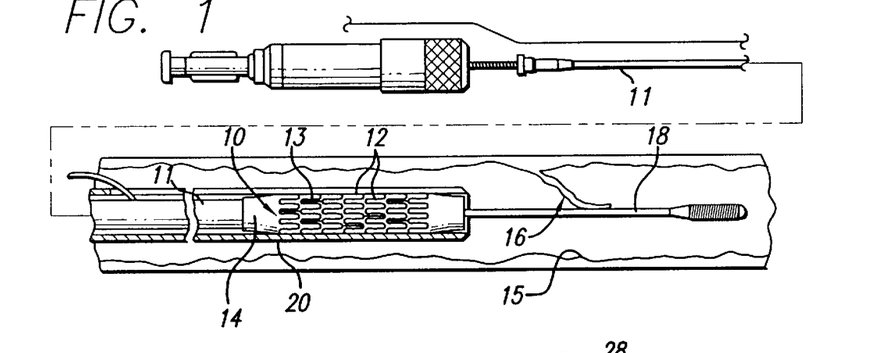
FIG. 1 is a side elevational view, partially in section, depicting a stent that has been crimped onto a delivery catheter and disposed within a vessel.

FIG. 1 illustrates intravascular stent 10 which is mounted onto delivery catheter 11. Stent 10 generally comprises a plurality of radially expandable cylindrical elements 12 disposed generally coaxially and interconnected by members 13 disposed between adjacent cylindrical elements 12. Delivery catheter 11 has an expandable portion or balloon 14 for expanding stent 10 within coronary artery 15 or other vessel such as saphenous veins, carotid arteries, arteries, and veins. Artery 15, as shown in FIG. 1, has dissected lining 16 which has occluded a portion of the arterial passageway.

Delivery catheter 11 onto which stent 10 is mounted is essentially the same as a conventional balloon dilatation catheter for angioplasty procedures. Balloon 14 may be formed of suitable materials such as polyethylene, polyvinyl chloride, polyethylene terephthalate, nylon and other like polymers. In order for stent 10 to remain in place on balloon 14 during delivery to the site of the damage within artery 15, stent 10 is compressed onto balloon 14. This compressing step is known as crimping.

An optional retractable protective delivery sleeve 20 may be provided to further ensure that stent 10 stays in place on balloon 14 of delivery catheter 11 and to prevent abrasion of the body lumen by the open surface of stent 10 during delivery to the desired arterial location. Other means for securing stent 10 onto balloon 14 may also be used, such as providing collars or ridges on the ends of the working portion, i.e., the cylindrical portion of balloon 14.

In order to implant stent 10, it is first mounted onto inflation balloon 14 on the distal extremity of delivery catheter 11. Stent 10 is crimped down onto balloon 14 to ensure a low profile. The present invention addresses this crimping procedure.

The catheter-stent assembly can be introduced into the patient's vasculature through processes known in the art. Briefly, guide wire 18 is disposed across the arterial section where an angioplasty or atherectomy has been performed requiring a follow-up stenting procedure. In some cases, the arterial wall lining may be detached so that guide wire 18 is advanced past detached or dissected lining 16 and the catheter-stent assembly is advanced over guide wire 18 within artery 15 until stent 10 is directly under detached lining 16. Prior to inflation of balloon 14, delivery sleeve 20 is retracted to expose stent 10. Depending on the balloon and stent assembly, a delivery sleeve may be unnecessary. Balloon 14 of delivery catheter 11 is then inflated using an inflation fluid. Expansion of balloon 14 in turn expands stent 10 against artery 15. Next, balloon 14 is deflated and catheter 11 is withdrawn leaving stent 10 to support the damaged arterial section. As mentioned above, in order to ensure proper seating of stent 10 on balloon 14, and to ensure proper deployment of stent 10 at the site of the damage within artery 15, the stent crimping procedure is important.

Figures 2, 3:
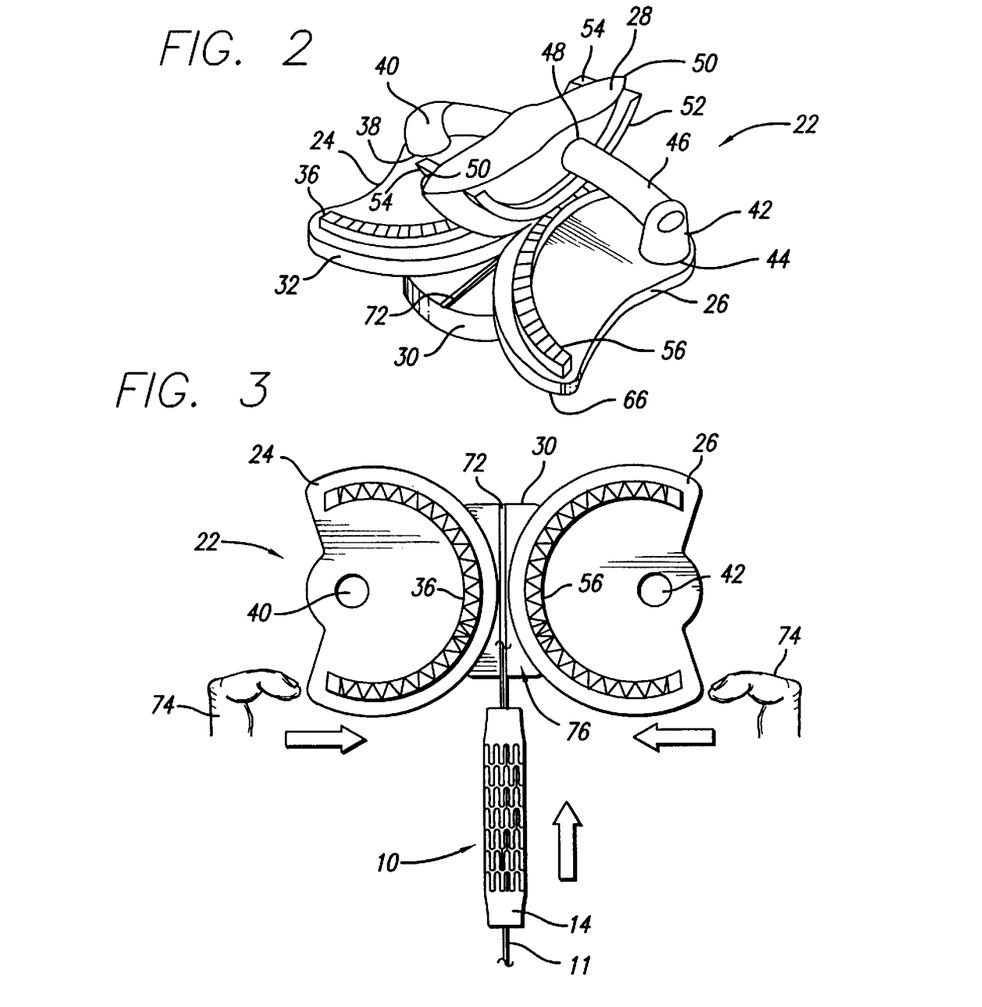
FIG. 2 is a perspective view of a preferred embodiment of the present invention stent crimping tool employing three orthogonally arranged cams.
FIG. 3 is a top plan view omitting the vertical cam to reveal the operation of the two side-by-side, opposed cams just prior to the crimping of a stent.

FIG. 2 is a perspective view of a preferred embodiment of the present invention stent crimping tool 22. As recognized in this perspective view, the present invention stent crimping tool 22 is characterized by three cams arranged orthogonally on a flat base plate. In particular, stent crimping tool 22 comprises first and second horizontal cams 24, 26 and third vertical cam 28, all arranged in an overlying relationship above base 30. The arrangement enables rotation of cams 24, 26, 28 in unison by use of interacting surfaces described below.

Figures 5A, 5B, 5C, 6:
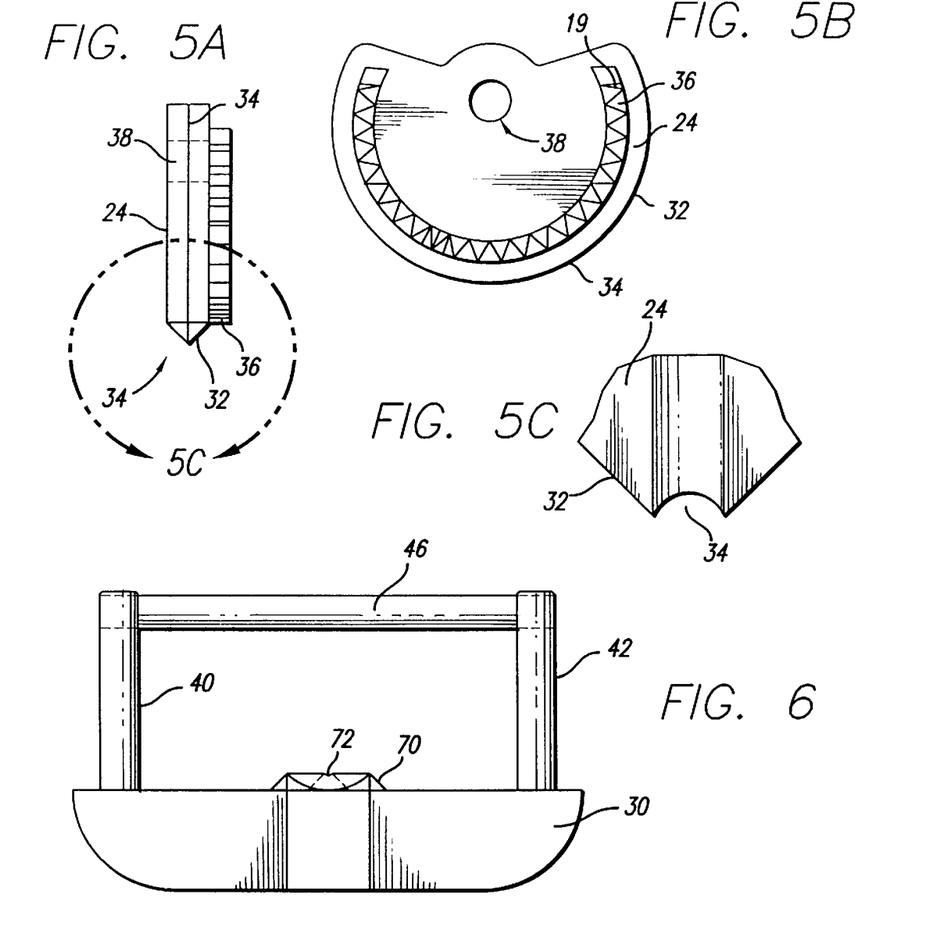

FIGS. 5A and 5B provide a side elevational and a plan view, respectively, of a preferred embodiment first horizontal cam 24. First horizontal cam 24 and second horizontal cam 26 are preferably identical. As seen in FIG. 2, both cams 24, 26 lie in a common horizontal plane.

As best seen in FIGS. 5A and 5B, first horizontal cam has a generally semi-circular shape with optional semi-circular edges 32. In fact, semi-circular edge 32 can be chamfered or beveled in alternative embodiments. Coinciding with edge 32 at an outer first circumference is groove 34, which is depicted in the enlarged detail view of FIG. 5C. Groove 34 preferably has a quarter-circle profile that is meant to engage the outside diameter of an uncrimped stent.

On one side of first horizontal cam 24 is rack 36. Rack 36 is located at a second circumference having a shorter radius. Rack 36 is optionally made from gear teeth 19 for engagement with another rack of like design. The specific construction of gear teeth 19 is known in the art. In an alternative embodiment (not shown), gear teeth 19 can be replaced with a roughened surface for frictional engagement with the roughened surface of a rack on an opposing cam.

Preferably at a center point or focus of first horizontal cam 24 is through hole 38, used for mounting cam 24 to base 30. As seen in FIG. 2, each horizontal cam 24, 26 is mounted to base 30 by passing upright posts 40, 42 through holes 38, 44. FIG. 6 provides a front elevational view of base 30 showing upright posts 40, 42. Connected to upright post 40, 42 is crossbar 46. Naturally, crossbar 46 and upright posts 40, 42 can be either manufactured in one piece or in separate pieces that are assembled as shown.

Crossbar 46 is used to support optional third vertical cam 28 as shown in FIG. 2. Third vertical cam 28 has a construction similar to first horizontal cam 24, shown in FIGS. 5A and 5B. To be sure, third vertical cam 28 has hole 48 through which crossbar 46 passes. Third vertical cam 28 also has a preferably semi-circular shape and further includes groove 50 at an outer circumference having a quarter circle profile, similar to the detail view of FIG. 5C.

A feature distinguishing third vertical cam 28 from horizontal cams 24, 26 is the presence of racks 52, 54. All three cams 24, 26, 28 are rotatably mounted to their respective supports and are free to turn. On the other hand, racks 52, 54 of third vertical cam 28 engage rack 36 and rack 56 of first horizontal cam 24 and second horizontal cam 26, respectively. Through this mechanical engagement, the motion of all three cams 24, 26, 28 are synchronized so that rotation of one cam causes rotation of the other two cams. All three cams 24, 26, 28 are mounted to base 30 by use of the support structure shown in FIG. 6.

Figure 7:
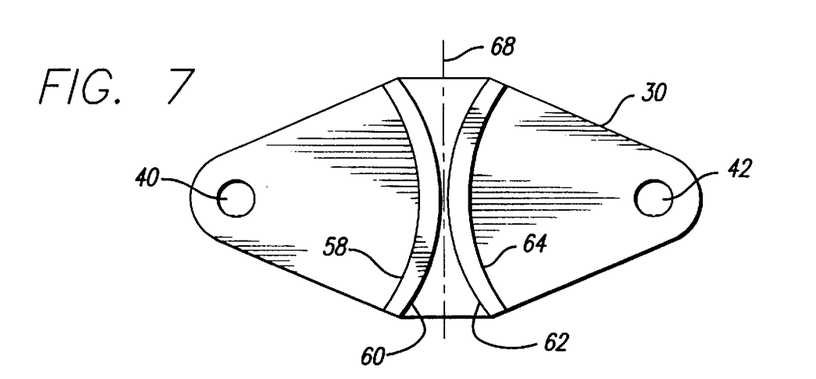
FIG. 7 is a plan view of the base shown in FIG. 6.

FIG. 7 is a simplified plan view of base 30 shown in FIG. 6. Crossbar 46 has been omitted for clarity. In this plan view, curved lines 58, 60, 62, and 64 coincide with the possible locations of outer edge 32 of first horizontal cam 24 and outer edge 66 of second horizontal cam 26, shown in FIG. 2, depending on the radius of each cam. Therefore, in the plan view of FIG. 7, curved lines 58, 60, 62, 64 provide an indication of the possible gap between the two side-by-side mounted first and second horizontal cams 24, 26.

In the preferred embodiment, tangent line 68 coincides with the tangents of first and second horizontal cams 24, 26 at a minimal distance between the cams. This minimal distance or gap between horizontal cams 24, 26 that is coextensive with tangent line 68 can be adjusted by moving posts 40, 42 or changing the radius of the respective cams.

FIG. 6 also depicts raised portion 70 having groove 72 extending thereon. Accordingly, as seen in FIG. 2, cams 24, 26, and 28 are oriented along groove 72, which coincides with tangent line 68. As mentioned earlier, a groove is formed into the outer edge or circumference of each cam 24, 26, 28, which grooves with groove 72 collectively form axial space 76 that spans a minimum distance among the three cams. Axial space 76 is also the imaginary intersection of the three cams 24, 26, 28. Each groove has preferably a quarter circle cross-sectional shape thereby forming a complete circle at the axial space.

Figure 9A:
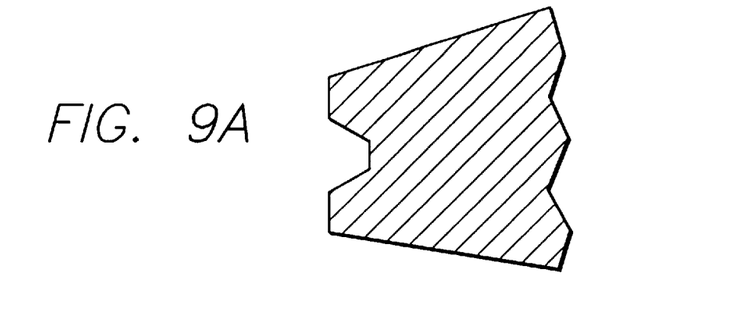
FIGS. 9A and 9B are partial sectional views of alternative embodiment cam grooves having a tapered cross-section and a mottled cross-section.
Figure 9B:
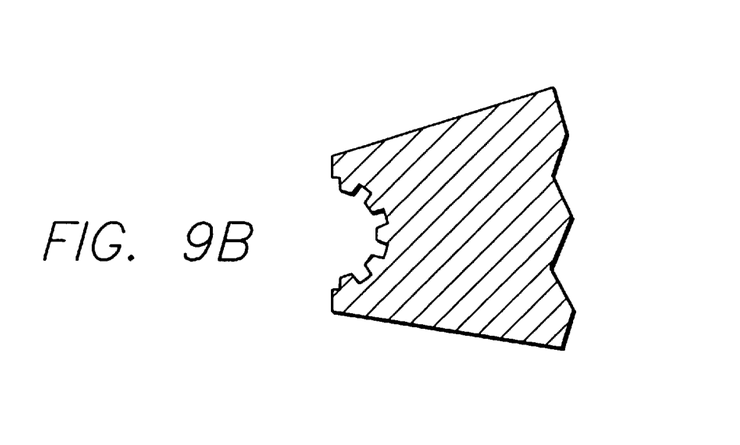

FIGS. 9A and 9B are exemplary embodiments of various other cross-sectional shapes of the groove of each cam. Specifically, FIG. 9A shows a tapered groove while FIG. 9B shows a mottled groove. The mottled groove has raised contours or bumps. Because the grooves are used to pinch uncrimped stent 10 onto balloon catheter 11, the surface texture or shape such as that shown in FIGS. 9A and 9B can be imparted into stent 10 during the crimping process. Profiles and shapes other than that shown in FIGS. 9A and 9B are possible and are contemplated. Furthermore, the arc defined by the curvature of the groove can range from, for example, a 60 degree arc for a six-cam arrangement to a 180 degree arc for a two-cam arrangement. Also, the groove of each cam can be coated or lined with an elastomeric material such as rubber.

FIG. 3 and FIGS. 4A, 4B and 4C illustrate the preferred crimping process for applying the present invention crimping tool 22. FIG. 3 is a plan view of the present invention crimping tool 22 wherein crossbar 46 and third vertical cam 28 have been omitted for clarity of illustration. In this plan view, stent crimping tool 22 is operated by user's fingers 74 pushing on first and second horizontal cams 24, 26. As mentioned earlier, the motion of horizontal cams 24, 26 is controlled through racks 36, 56 and their engagement with racks 52, 54 of vertical cam 28 so that all three cams rotate in unison. Groove 72 of base 30 is shown coinciding with tangent 68 shown in FIG. 7. Groove 72 passes through axial space 76. The user mounts uncrimped stent 10 onto delivery catheter 11 and slowly advances the stent-balloon assembly forward toward axial space 76, denoted in FIG. 3 by a circle.

Figures 4A, 4B, 4C:
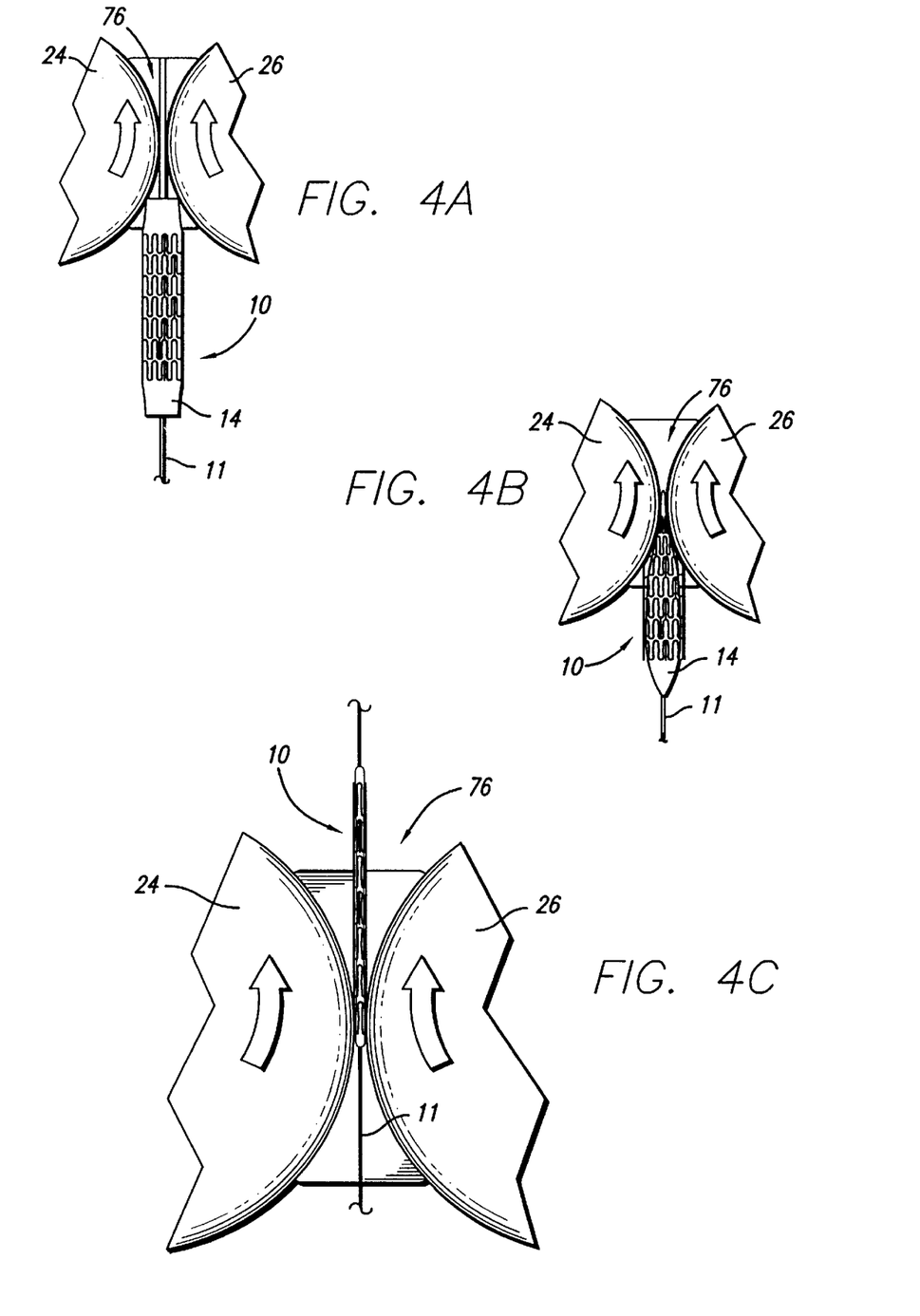
FIGS. 4A, 4B, and 4C are plan views showing the stent loaded onto a balloon catheter and passing the stent-catheter assembly through the axial space formed by the grooves.

FIG. 4A is a partial plan view depicting the stent-catheter assembly just prior to engagement with the outer circumference of horizontal cams 24, 26. Actually, it is the groove of each respective cam that engages stent 10. The grooves, however, have been omitted from the figures for clarity.

FIG. 4B shows the crimping process as the stent-catheter assembly passes into axial space 76, which has a smaller diameter than the uncrimped stent. As a result, first and second horizontal cams 24, 26 pinch crimp 10 onto balloon 14 in the horizontal plane.

Importantly, a mandrel (not shown) should be placed in the guide wire lumen (not shown) within balloon 14 before the crimping process to support crimped stent 10 from underneath. The finished diameter of crimped stent 10 is determined by the amount of pressure exerted by horizontal cams 24, 26 and the diameter of the internal mandrel.

FIG. 4C shows the crimping procedure continuing wherein first and second horizontal cams 24, 26 have crimped the entire length of intravascular stent 10; indeed, the stent-catheter assembly has passed almost entirely through axial space 76. The arrows in FIGS. 4A, 4B and 4C indicate the direction of rotation of first and second horizontal cams 24, 26 in order to pass the stent-catheter assembly through axial space 76.

By counter-rotating cams 24, 26 while the stent-catheter assembly is in the position shown in 4C, the stent-catheter assembly can be withdrawn through axial space 76 in the opposite direction. Thus, stent 10 can be crimped onto balloon 14 in either direction. Furthermore, to ensure an even circumferential crimp, the stent-catheter assembly can be manually rotated about its longitudinal axis by the user as the assembly is crimped in the axial space 76.

In the exemplary embodiment shown in FIG. 2, first and second horizontal cams 24, 26 apply pressure to stent 10 at the 0° and 180° positions while third vertical cam 28 and raised portion 70 with groove 72 apply pressure in the 90° and 270° positions. The application of radial forces at the various angular positions are only exemplary. It is contemplated that the cams be relocated or more cams added to provide radial forces from different or addition angular positions.

Figure 8A:
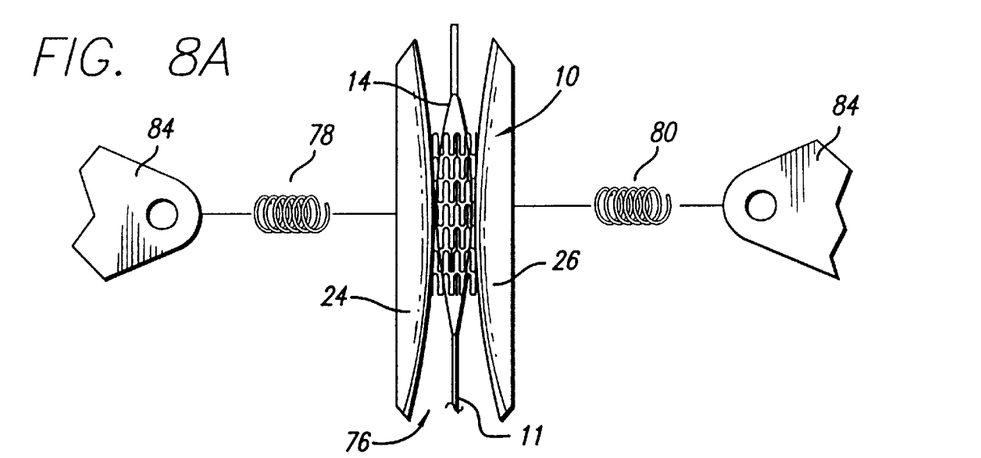
FIGS. 8A, 8B, 8C, and 8D illustrate an alternative embodiment for the present invention stent crimping tool.
Figure 8B:
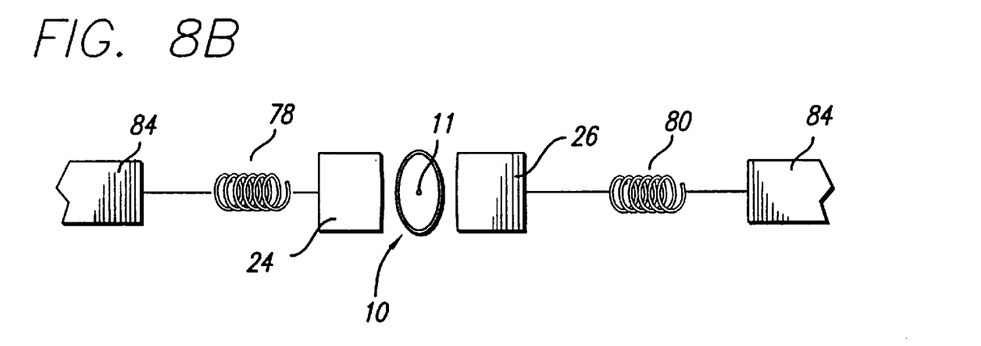

FIGS. 8A, 8B, 8C, and 8D are simplified schematic diagrams of an alternative embodiment of the present invention. In FIG. 8A, opposed first and second horizontal cams 24, 26 are biased by linear springs 78, 80, torsion springs, elastic bands or the like, toward each other as seen in this plan view. When the stent-catheter assembly is inserted into axial space 76, rotation of cams 24, 26 as well as the expansion force from springs 78, 80 push cams 24, 26 into stent 10, consequently crimping stent 10 onto balloon 14. This action is seen in the front elevational view of FIG. 8B.

Figure 8C:
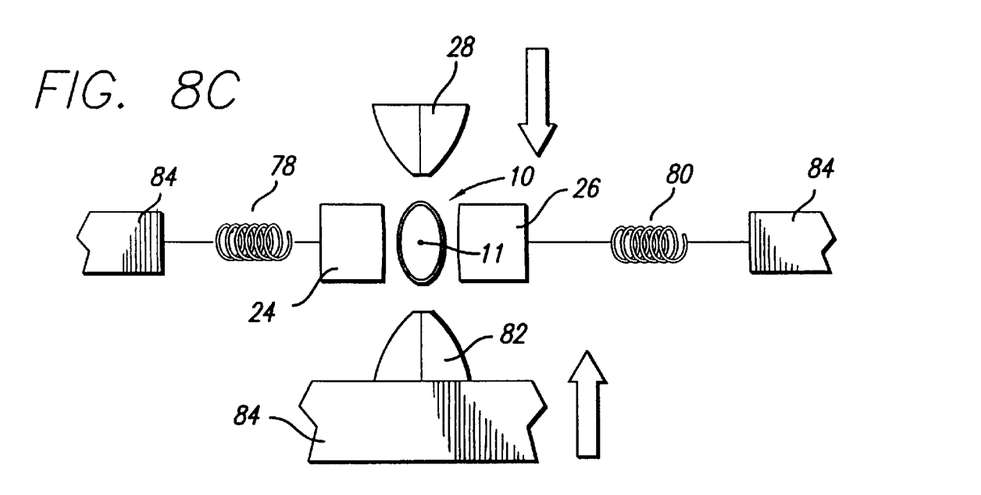

FIG. 8C provides a front elevational view of an alternative embodiment wherein third vertical cam 28 is shown along with counteracting fourth vertical cam 82. Cams 28, 82 act in unison to apply radial forces from the 90° and 270° positions around stent 10 while cams 24, 26 apply compressive forces from the 0° and 180° positions around stent 10. Importantly, the process of applying the crimping forces in the horizontal plane by cams 24, 26 and in the vertical plane by cams 28, 82 can occur sequentially or simultaneously.

Figure 8D:
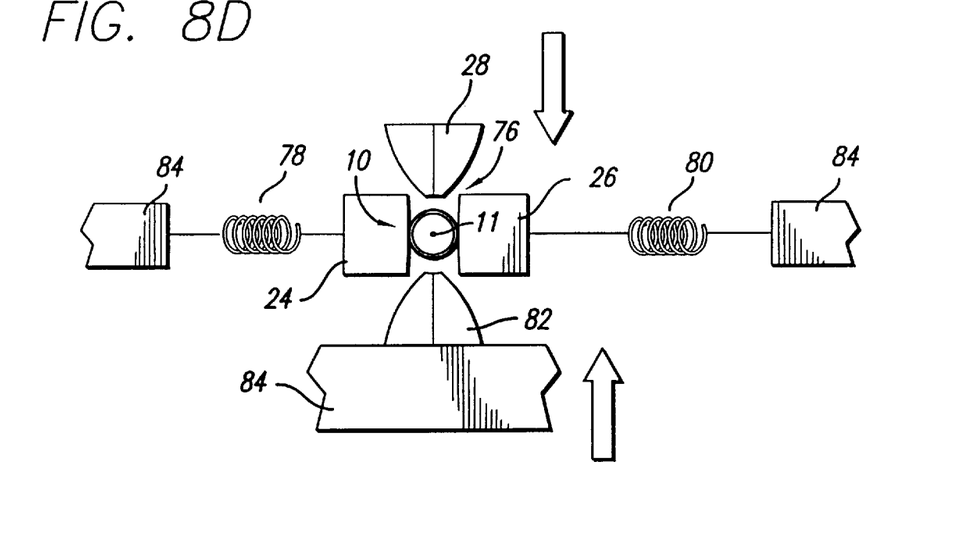

As seen in the front elevational view of FIG. 8D, when all four cams 24, 26, 28 and 82 completely converge, they form axial space 76 and their grooves entirely circumscribe the stent-catheter assembly. From this end view, it is clear that by completely circumscribing the stent-catheter assembly, the present invention is able to evenly and homogeneously crimp stent 10 onto balloon 14. Bearing in mind that cams 24, 26, 28 and 82 rotate in unison, or at least in opposed pairs, the stent-catheter assembly can be passed through axial space 76 several times to further ensure homogeneous and uniform crimping.

In this alternative embodiment, an interacting rack/gear teeth system can be used as in the embodiment shown in FIG. 2. Each cam can be supported on base 84 similar to the construction shown in FIG. 2.

The present invention crimping tool 22 is preferably made from injection molded plastics or machined from a variety of polymers including DELRIN or TEFLON. In alternative embodiments, rubber cams can be used. To withstand the rigors of high production rates, the present invention crimping tool can be constructed from stainless steel, brass, aluminum, or the like. Lighter metals or high strength rigid plastics can be use for portable units.

The present invention crimping tool 22 can be immersed in a fluid at a variety of temperatures of pressures, either of which is held at a steady state or is varied over time. Of course, the tool is easily adaptable to automation.

Although the exemplary embodiments described above rely on three to four orthogonally arranged cams to perform the crimping process, it is contemplated that fewer or more cams can be used to sequentially or simultaneously perform the crimping process. Moreover, the vertically oriented cams can be tilted slightly to engage the horizontal cams at an oblique angle rather than the right angle shown in FIG. 2 or FIG. 8C. For example, a six-cam arrangement (not shown) can have two horizontal cams with the remaining four cams all spaced apart at 60 degree intervals. Hence, this embodiment would have vertically oriented cams tilted at an angle. In addition, one or more cams may have toothed racks optionally stacked or use frictional engagement racks that permit the cams to rotate together.

In yet another embodiment (not shown), an optional funnel-like clip or the like can be mounted to base 30 at the entrance of axial space 76 in the embodiment shown in FIG. 2 to help align and guide the stent-catheter assembly into the rotating cams. With use of the clip, one of the user's hands is freed to perform other duties.

The present invention is sterilized and intended to be used in a cath lab by a trained technician or cardiologist. More precisely, as will be appreciated by those skilled in the art, the present invention crimping tool 22 is designed both for single use applications in a cath lab by a physician, or for multiple use applications in a sterile environment in a high volume manufacturing facility. In such a manufacturing facility where sterile conditions exist, stent crimping tool 22 can be used repeatedly to crimp stents onto balloons until the mechanism wears out. Thus, repeated uses of the present invention are contemplated for controlled, sterile environments, as are single use applications when operated by cath lab personnel.

Furthermore, the present invention crimping tool can be used with any stent that is released without a delivery system. The crimping tool may also be sold alone, because its design is robust enough to undergo many uses.

Other modifications can be made to the present invention without departing from the scope thereof. The specific dimensions, procedural steps, and materials of construction are provided as examples, and substitutes are readily contemplated which do not depart from the invention.

What is claimed is:

1. A tool for crimping a stent onto a balloon catheter, comprising:
   a base having a central groove;
   first and second semicircular cams that rotate side-by-side within a common horizontal plane and having a gap therebetween, wherein each cam is rotatably supported in an overlying position above the base, and wherein each cam has a groove at a respective outer circumference;
   a vertically disposed third cam contained in a generally vertical plane intersecting the horizontal plane containing the first and second cams, wherein the third cam includes a tangent line coextensive with the gap between the first and second semicircular cams, and wherein the third cam is rotatably attached to and overlying the base and engages the first and second cams at a circumference, and wherein the third cam includes a groove at an outer circumference;
   wherein the grooves of the cams and in the base collectively form an axial space coextensive with the gap and tangent line;
   whereby the stent loaded on to the balloon catheter is inserted into the axial space and rotation of the cams collectively crimp the stent onto the catheter.

2. The crimping tool of claim 1, wherein the first and second cams each have toothed racks at a circumference on a top surface, and the third cam includes toothed racks at a circumference on one side and on an obverse side, and wherein the toothed rack of the third cam on one side engages the toothed rack of the first cam, and the toothed rack on the obverse side engages the toothed rack of the second cam.

3. The crimping tool of claim 1, wherein the third cam has a semicircular shape.

4. The crimping tool of claim 1, wherein the central groove of the base is raised from a top surface of the base.

5. The crimping tool of claim 1, wherein each cam includes a mating surface that is chamfered.

6. The crimping tool of claim 1, wherein the stent and catheter are encased in a sleeve.

7. The crimping tool of claim 1, wherein the groove of each cam has a quarter-circle cross-sectional shape.

8. The crimping tool of claim 1, wherein at least one of the grooves is tapered.

9. The crimping tool of claim 1, wherein at least one of the grooves is mottled.

10. The crimping tool of claim 1, wherein the first and second cams are biased together.

11. The crimping tool of claim 1, wherein the base includes a fourth semicircular cam coplanar with the third cam in the vertical orientation, and wherein the fourth cam includes a groove at an outer circumference that is aligned with the raised groove of the base.

12. The crimping tool of claim 1, wherein the vertical plane intersects the horizontal plane at a right angle.

13. The crimping tool of claim 1, wherein the vertical plane intersects the horizontal plane at an oblique angle.

14. A tool for crimping a stent onto a balloon catheter, comprising:
   a base having a raised central groove separating spaced apart first and second upright posts;
   a first semicircular cam having a groove formed at an outer circumference, wherein the first cam is rotatably mounted on the first post in a horizontal orientation;
   a second semicircular cam having a groove formed at an outer circumference, wherein the second cam is rotatably mounted on the second post in a horizontal orientation, wherein the first and second cams are oriented in a common plane and have a gap therebetween;
   a horizontal cross bar connecting the first post to the second post overlying the base;
   a third cam rotatably mounted on the cross bar in a generally vertical orientation, wherein the third cam includes a groove at an outer circumference and having a tangent line coextensive with the gap, and wherein the third cam engages the first and second cams;

an axial space formed collectively by the grooves of each cam;

whereby when the stent loaded on to the catheter is inserted into the axial space, and the cams are rotated, the stent is crimped onto the catheter.

15. The crimping tool of claim 14, wherein each groove of the cams is defined by at most a 180° arc.

16. The crimping tool of claim 14, wherein each cam comprises a metal selected from the group consisting of stainless steel, brass, or aluminum.

17. A tool for crimping a stent onto a balloon catheter, comprising:

a base having a raised central groove;

a plurality of semicircular cams each having a groove formed at an outer circumference, wherein the plurality of cams are rotatably mounted on the base, and wherein the cams are oriented to collectively form an axial space defined by the raised central groove and the grooves of each cam; and a rack affixed to each cam engaging the rack of an adjacent cam for synchronized rotation of the cams;

whereby when the stent loaded on to the catheter is inserted into the axial space, and the cams are rotated, the stent is crimped onto the catheter.

18. The crimping tool of claim 17, wherein the tool includes at least three cams.

19. The crimping tool of claim 17, wherein the tool includes at least four cams.

20. The crimping tool of claim 17, wherein the tool includes greater than four cams.

21. The crimping tool of claim 17, wherein the tool includes a first cam having a larger diameter than a second cam.

22. The crimping tool of claim 17, wherein at least one of the cams includes an elastomeric coating on the groove.

23. The crimping tool of claim 17, wherein at least one of the cams includes a rubber coating on the groove.

24. The crimping tool of claim 17, wherein the rack includes a frictional surface engaging the frictional surface of the adjacent rack.

25. The crimping tool of claim 17, wherein the cams are fabricated to different sizes.

* * * * *

UNITED STATES PATENT AND TRADEMARK OFFICE
CERTIFICATE OF CORRECTION

PATENT NO. : 6,082,990
DATED : Jul. 4, 2000
INVENTOR(S) : Gregg A. Jackson, Stephen A. Morales

It is certified that error appears in the above-identified patent and that said Letters Patent is hereby corrected as shown below:

Title page, under "U.S. DOCUMENTS", delete the following
     patents: "3,439,519,
             4,538,440,
             4,703,546,
             5,207,960,
             5,658,181".

Signed and Sealed this

Tenth Day of April, 2001

*Attest:*

NICHOLAS P. GODICI

*Attesting Officer*     Acting Director of the United States Patent and Trademark Office